(12) United States Patent
Lekholm et al.

(10) Patent No.: US 11,866,711 B2
(45) Date of Patent: Jan. 9, 2024

(54) X-APTAMERS FOR THE USE IN DETECTION OF SNAP25

(71) Applicant: Galderma Holding S.A., La Tour-de-Peilz (CH)

(72) Inventors: Emilia Lekholm, Uppsala (SE); Erica Forsberg, Uppsala (SE); Kimia Hosseini, Uppsala (SE); Robert Fredriksson, Uppsala (SE); Anh-Tri Do, Uppsala (SE)

(73) Assignee: GALDERMA HOLDING SA, Zug (CH)

( * ) Notice: Subject to any disclaimer, the term of this patent is extended or adjusted under 35 U.S.C. 154(b) by 36 days.

(21) Appl. No.: 17/458,169

(22) Filed: Aug. 26, 2021

(65) Prior Publication Data

US 2022/0064648 A1    Mar. 3, 2022

Related U.S. Application Data

(60) Provisional application No. 63/071,672, filed on Aug. 28, 2020.

(51) Int. Cl.
*C12N 15/115* (2010.01)
*G01N 33/68* (2006.01)

(52) U.S. Cl.
CPC ....... *C12N 15/115* (2013.01); *G01N 33/6872* (2013.01); *G01N 2333/705* (2013.01)

(58) Field of Classification Search
CPC .................. C12N 15/115; C12N 2310/16
See application file for complete search history.

(56) References Cited

U.S. PATENT DOCUMENTS

| | | | |
|---|---|---|---|
| 2014/0100120 | A1 | 4/2014 | Gorenstein et al. |
| 2016/0003824 | A1 | 1/2016 | Broide et al. |

FOREIGN PATENT DOCUMENTS

| | | | |
|---|---|---|---|
| CN | 113817741 A | * | 12/2021 |
| WO | WO-2018/005974 | | 1/2018 |

OTHER PUBLICATIONS

English Machine translation of CN113817741A, pp. 1-20. Bi et al. (Year: 2021).*

International Search Report and Written Opinion issued for PCT Appl. Ser. No. PCT/IB2021/057845 dated Nov. 24, 2021 (250 pages).

Rohloff et al. "Nucleic acid ligands with protein-like side chains: modified aptamers and their use as diagnostic and therapeutic agents.", Molecular Therapy-Nucleic Acids, vol. 3, 2014: e201 (13 pages).

* cited by examiner

*Primary Examiner* — Brian Whiteman
(74) *Attorney, Agent, or Firm* — Sunit Talapatra; Foley & Lardner LLP

(57) ABSTRACT

Described are methods for utilizing X-aptamers for detecting human SNAP25 and fragments thereof, and compositions comprising the X-aptamers.

19 Claims, 8 Drawing Sheets

Specification includes a Sequence Listing.

FIG. 1

Peptide 1 (SEQ ID NO:97)   WGNNQDGVVASQPARVVDEREQMAISGGFIRRVTN

Peptide 2 (SEQ ID NO:98)   LADESLESTRRMLQLVEESKDAGIRTLVMLDEQGEQL

Peptide 3 (SEQ ID NO:99)   QNRQIDRIMEKADSNKTRIDEANQRATKMLGSG

Peptide 4 (SEQ ID NO:100)  QNRQIDRIMEKADSNKTRIDEANQ

SNAP25 (SEQ ID NO:101)

MEQKLISEEDLMAEDADMRNELEEMQRRADQLADESLESTRRMLQLVEE

SKDAGIRTLVMLDEQGEQLERIEEGMDQINKDMKEAEKNLTDLGKFCGL

CVCPCNKLKSSDAYKKAWGNNQDGVVASQPARVVDEREQMAISGGFIRR

VTNDARENEMDENLEQVSGIIGNLRHMALDMGNEIDTQNRQIDRIMEKA

DSNKTRIDEANQRATKMLGSGDYKDDDDK

X-APTAMERS FOR THE USE IN DETECTION OF SNAP25

CROSS-REFERENCE TO RELATED APPLICATIONS

This application is a U.S. non-provisional application which claims a priority benefit to U.S. Provisional Application No. 63/071,672, filed Aug. 28, 2020; the entirety of which is herein expressly incorporated by reference.

FIELD OF THE INVENTION

The present disclosure relates to the field of X-aptamers, synthetic affinity reagents that incorporate naturally and chemically modified nucleic acids, for detecting human SNAP-25

SEQUENCE LISTING

The instant application contains a Sequence Listing which has been submitted electronically in ASCII format and is hereby incorporated by reference in its entirety. Said ASCII copy, created on Nov. 3, 2021, is named 105153-0311_SL.txt and is 81,097 bytes in size.

BACKGROUND

Aptamers are structurally distinct RNA and DNA oligonucleotides that can mimic protein-binding molecules and exhibit high (nM) binding affinity based on their unique secondary three-dimensional structure conformations and not by pair-wise nucleic acid binding. Aptamers can be selected via high-throughput in vitro methods to bind target molecules. Aptamers are thus emerging as viable alternatives to small molecules and antibody-based therapies in the field of drug development.

Aptamers are typically ~1/10th the molecular weight of antibodies, yet they provide complex tertiary folded structures with sufficient recognition surface areas to rival those of antibodies. Aptamers achieve their selectivity through a very limited repertoire of functional groups—the sugar phosphate backbone and 4 bases. In contrast antibodies use all 20 amino acids with a full range of chemical substituents including positively-charged, sulfhydryl, hydrophobic sidechains, etc. Aptamers are polyanions, potentially limiting their affinity towards the full diversity of proteins. It can be difficult to select an aptamer targeted to very acidic proteins because there are no cationic groups to neutralize anionic surfaces on the protein. While oligonucleotide agents show therapeutic promise, various pharmacological problems must be overcome. High sensitivity to nuclease digestion makes oligonucleotide agents unstable and thus impracticable for in vivo administration by either intravenous or oral routes.

In fact, a diverse range of modifications at all possible modification sites of an oligonucleotide have been reported for enhancing oligonucleotide drug properties, including in vivo stability. These include alterations of linkages (backbones), heterocycles, carbohydrates, and connection and conjugation sites, as well as the complete removal of the sugar-phosphate backbone.

While antibodies raised to particular antigens have been utilized for years in detecting any number of antigens, there can be a host of variations, both major and minor, between different batches of antibodies that can prove problematic to good manufacturing practices that rely upon the continuity of antibodies from batch to batch to create a product. Furthermore, production of aptamers are approximately 100-fold less expensive that antibodies.

Efforts to combine the best attributes of antibodies and aptamers have been elusive. Selection of aptamers by the classical iterative selection-amplification method followed by post-selection modification has been disappointing because the modifications affect the three dimensional structure of the aptamer, which is the basis of its ability to bind to the target by which it was selected. It has been shown that certain substituents can be introduced into the bases of the oligonucleotides to provide additional functionalities. For instance, the 5-position of dU can be replaced with a range of substituents (X) and still allow Taq and other polymerases to amplify the selected sequences. Thus, with the appropriate 5-X-dUTP, it is possible to amplify a selected sequence during the in vitro iterative SELEX scheme and create a large initial random library ($10^{14}$ different sequences), then select a subset that binds to the target protein, amplify and repeat this cycle—often 10-15 cycles are required. The problem is that each resulting 5-X-dU position ends up with the same modified X-substituent.

It is apparent that there is a need in the art for aptamers that have the flexibility and ease of use seen in antibodies, but lack the limitations of antibodies. The invention described herein provides novel compositions and methods for achieving this end, particularly with regard to human protein SNAP25.

SUMMARY OF THE DISCLOSURE

The present disclosure is generally drawn to X-aptamers that bind human SNAP25 and fragments thereof, and methods of utilizing the X-aptamers.

In some aspects, the disclosure is broadly drawn to synthetic oligonucleotide sequences selected from the group consisting of SEQ ID NOs:1-96.

In some aspects, the W symbol corresponds to a modified nucleotide comprising an indol, the X symbol corresponds to a modified nucleotide comprising an amine, and/or the Y symbol corresponds to a modified nucleotide comprising a phenol. In some aspects, the modified nucleotide is a deoxyuridine. In some aspects, the modified nucleotide is a deoxyribonucleotide triphosphate.

In some aspects, the oligonucleotide is bound to an additional molecule. In some aspects, the additional molecule is SNAP25 or a fragment thereof. In some aspects, the additional molecule is a nucleic acid sequence or an amino acid sequence. In some aspects, the additional molecule is a protein or an enzyme. In some aspects, the additional molecule is a quantum dot.

In some aspects, the additional molecule is a fluorescent molecule. In some aspects, the fluorescent molecule is a fluorescent protein. In some aspects, the additional molecule is a dye. In some aspects, the additional molecule is a chelator. In some aspects, the additional molecule is a linker capable of linking to another molecule.

In some aspects, the disclosure is broadly drawn to a composition comprising a synthetic oligonucleotide sequence selected from the group consisting of SEQ ID NOs:1-96.

In some aspects, the disclosure is broadly drawn to a kit comprising a synthetic oligonucleotide sequence selected from the group consisting of SEQ ID NOs:1-96.

In some aspects, the disclosure is broadly drawn to a method of isolating SNAP25, or a fragment thereof, the method comprising: (a) administering a composition comprising SNAP25, or a fragment thereof, to a composition comprising one or more synthetic oligonucleotide sequences selected from the group consisting of SEQ ID NOs:1-96, wherein the synthetic oligonucleotide sequences are immobilized; (b) washing impurities from the SNAP25 or the fragment thereof bound to the immobilized synthetic oligonucleotide; and (c) eluting the SNAP25 or the fragment thereof from the immobilized synthetic oligonucleotide sequences.

In some aspects, the disclosure is broadly drawn to a method of binding SNAP25, or a fragment thereof, with one or more X-aptamers, the method comprising administering a composition comprising one or more synthetic X-aptamers selected from the group consisting of SEQ ID NOs:1-96 to a composition comprising the SNAP25 or the fragment thereof, and wherein the one or more synthetic X-aptamers bind to the SNAP25 or the fragment thereof.

In some aspects, the composition comprising the SNAP25 or the fragment thereof is a composition in vivo. In some aspects, the composition comprising the SNAP25 or the fragment thereof is a composition in vitro. In some aspects, the composition comprising the SNAP25 or the fragment thereof is a composition in situ. In some aspects, the composition comprising the SNAP25 or the fragment thereof is a tissue sample. In some aspects, the composition comprising the SNAP25 or the fragment thereof is a tissue culture. In some aspects, the composition comprising the SNAP25 or the fragment thereof is a cell culture. In some aspects, the composition comprising the SNAP25 or the fragment thereof is a gel.

In some aspects, the one or more X-aptamers are bound to an additional molecule. In some aspects, the additional molecule is a nucleic acid sequence or an amino acid sequence. In some aspects, the additional molecule is a protein or an enzyme. In some aspects, the additional molecule is a quantum dot. In some aspects, the additional molecule is a fluorescent molecule. In some aspects, the additional molecule is a fluorescent protein. In some aspects, the additional molecule is a dye. In some aspects, the additional molecule is a chelator. In some aspects, the additional molecule is a magnetic particle. In some aspects, the additional molecule is a linker capable of linking to another molecule.

The following detailed description is exemplary and explanatory, and is intended to provide further explanation of the invention.

BRIEF DESCRIPTION OF THE FIGURES

FIG. 1 Identifies the sequences of Peptides 1-4 and SNAP25, wherein Peptides 1, 2, 3 (a fragment, not the entire Peptide 3), and 4 are represented as subsequences within SNAP25.

DETAILED DESCRIPTION

I. Definitions

Figure 2A:
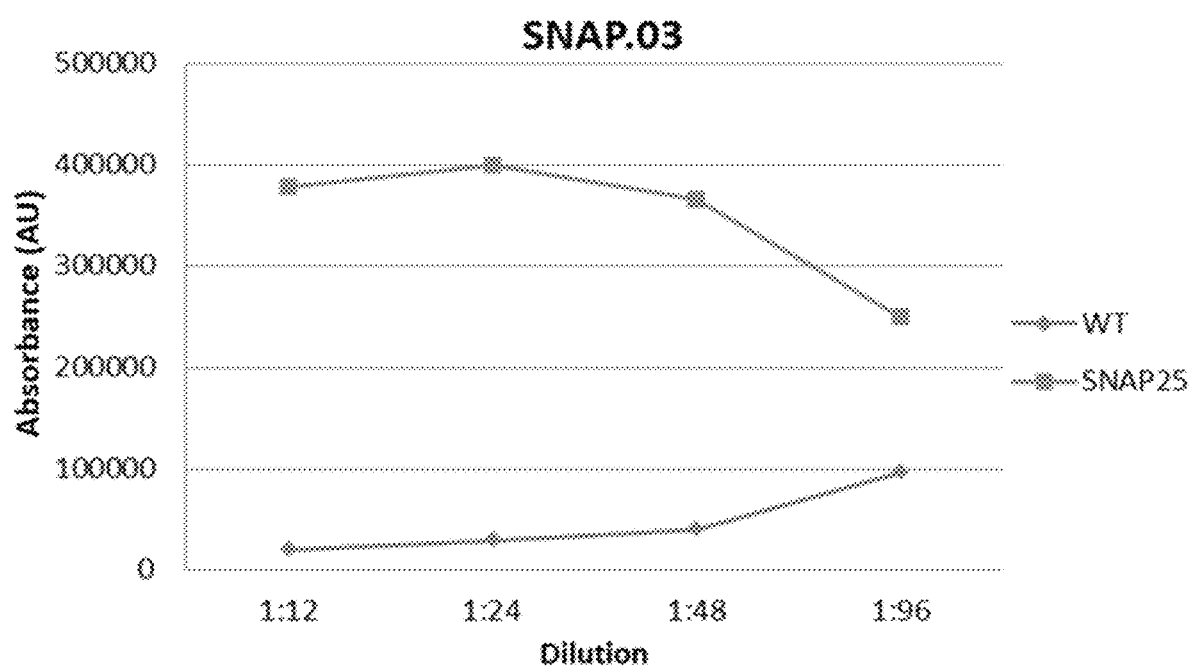
FIGS. 2A to 2E depicts X-aptamers SNAP0.3 (FIG. 2A), PEP1.02 (FIG. 2B), PEP2.01 (FIG. 2C), PEP2.02 (FIG. 2D), and PEP3.02 (FIG. 2E) tested as capture molecules in a sandwich ELISA using dilutions of protein samples from wt HEK cells ("wt", with no or low endogenous SNAP25 expression, diamond-pattern line), or HEK cells overexpressing SNAP25 (square-pattern line). High levels of binding were found X-aptamers in samples from HEK expressing SNAP25, while protein samples from wt HEK cells had low binding, indicating specificity towards SNAP25 and low affinity to other cellular proteins. The absorbance was measured at 450 nm.
Figure 2B:
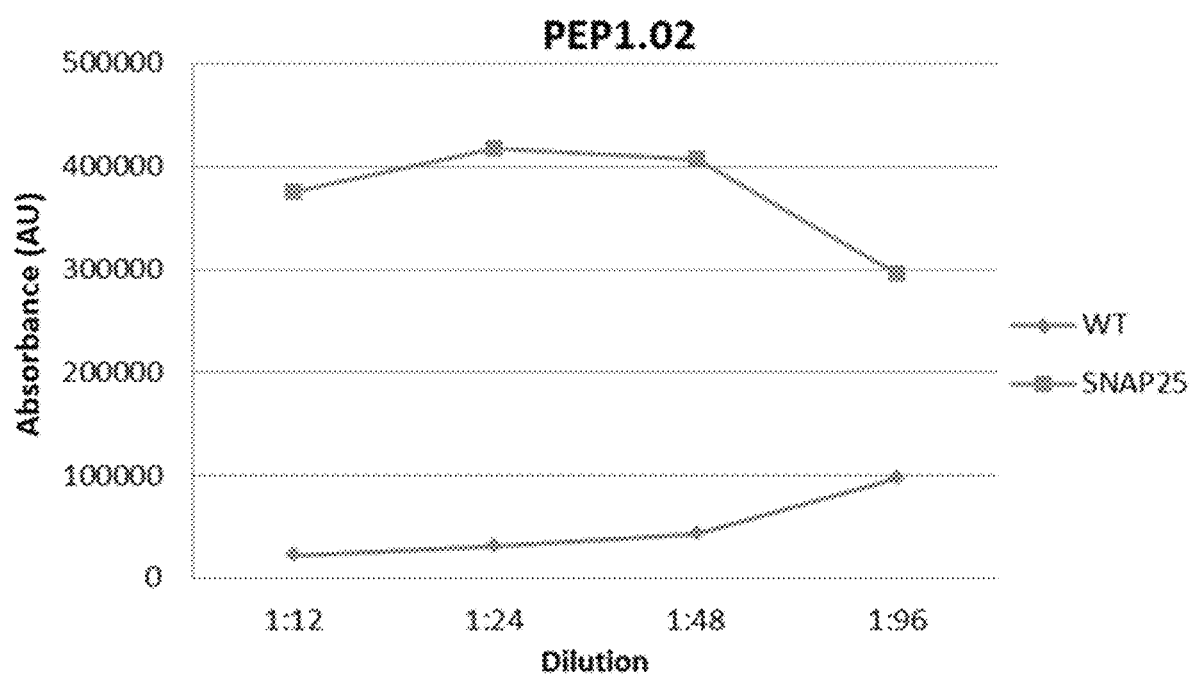
Figure 2C:
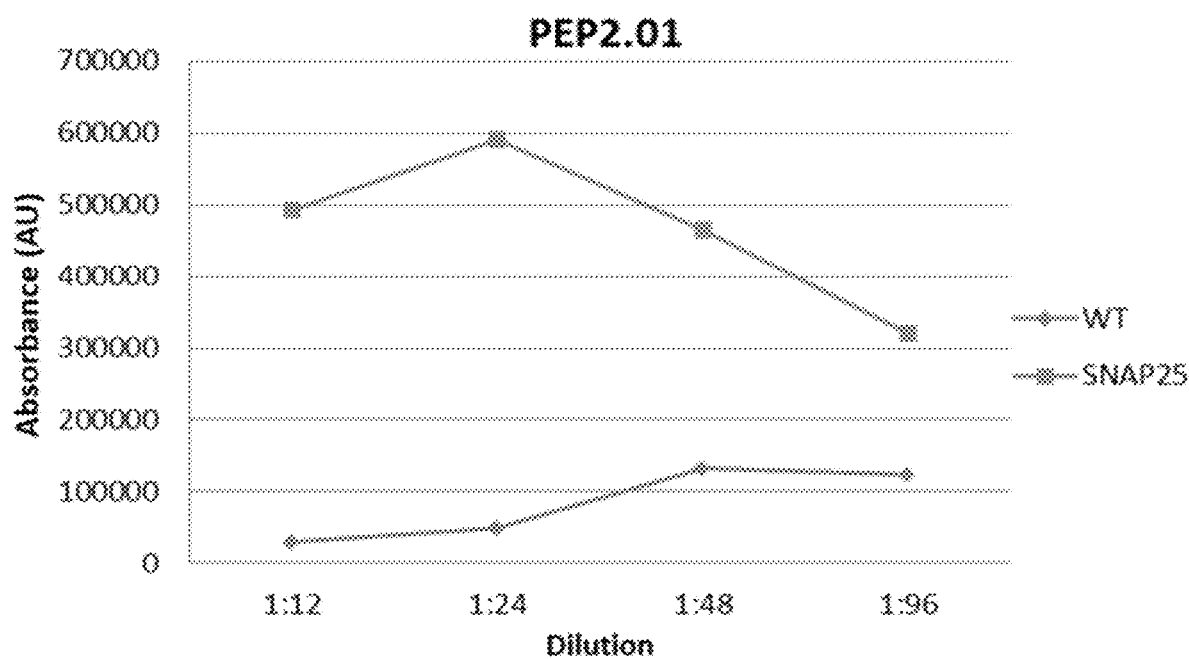
Figure 2D:
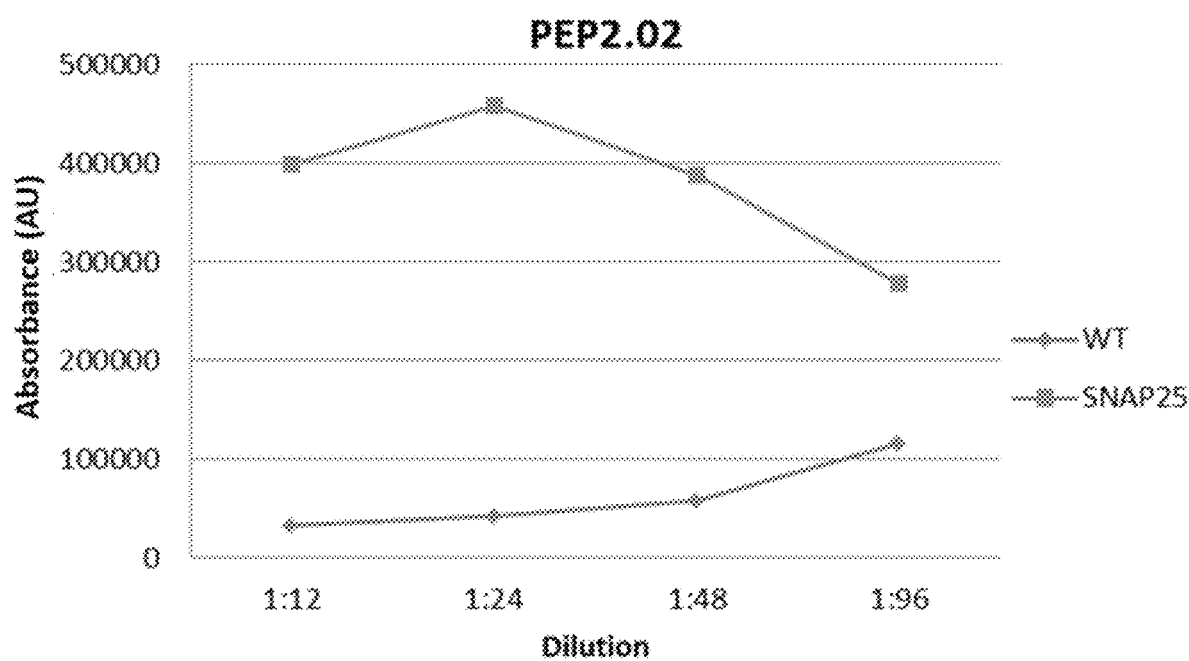
Figure 2E:
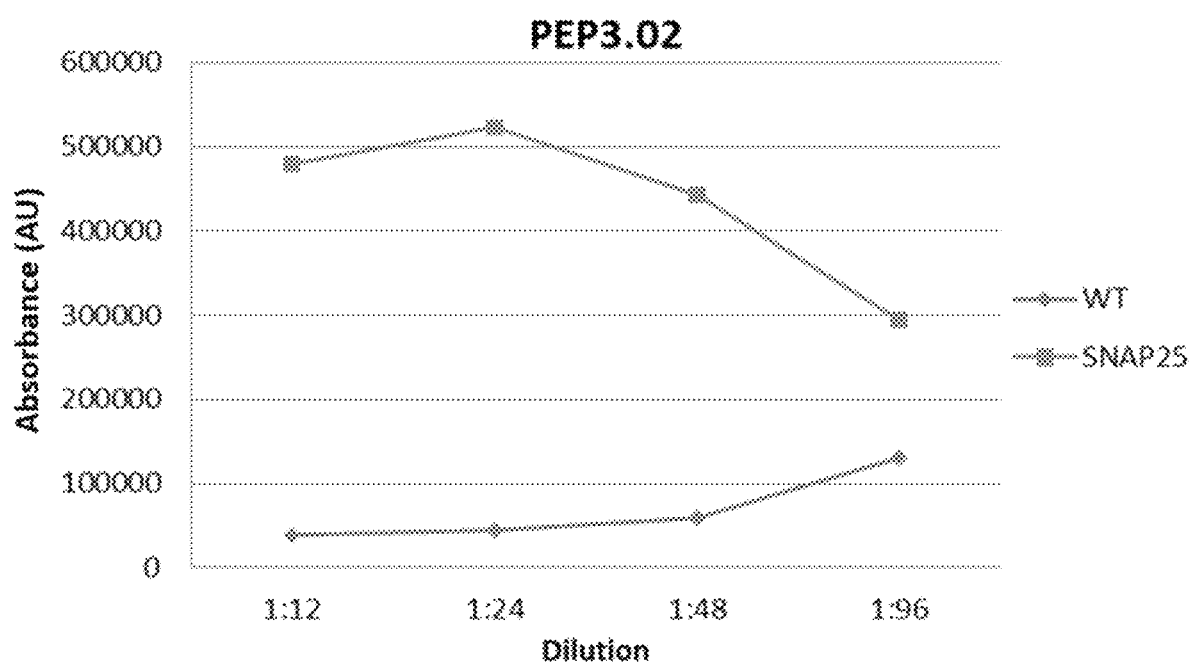

While the following terms are believed to be well understood by one of ordinary skill in the art, the following definitions are set forth to facilitate explanation of the presently disclosed subject matter.

The term "a" or "an" may refer to one or more of that entity, i.e. can refer to plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Reference throughout this specification to "one embodiment", "an embodiment", "one aspect", or "an aspect" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

As used herein, the terms "about" or "approximately" when preceding a numerical value indicates the value plus or minus a range of 10% of the value.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

As used herein, a "control" is an alternative sample used in an experiment for comparison purpose. A control can be "positive" or "negative." A "control sample" or "reference sample" as used herein, refers to a sample or reference that acts as a control for comparison to an experimental sample. For example, an experimental sample comprises compound A, B, and C in a vial, and the control may be the same type of sample treated identically to the experimental sample, but lacking one or more of compounds A, B, or C.

As used herein, "SNAP25" and "SNAP-25" refer to a peptide sequence, or fragment thereof, of a human SNAP25 protein (Entrez 6616; UniProt P60880).

As used herein, "botulinum toxin," "botulinum neurotoxin," and "BoNT" are used interchangeably to refer to any of the neurotoxic proteins produced by bacteria of genus *Clostridium*. The neurotoxic proteins include botulinum neurotoxin A, B, C, D, E, F, G, and H.

As used herein, "SELEX" refers to the iterative selection and amplification aptamer selection method described in 1990 by Tuerk and Gold (*Science*. (1990), 249(4968):505-510) and Ellington and Szostak (*Nature*. (1990), 346:818-822). As originally described, SELEX begins with a library of soluble oligonucleotides that is contacted with target compounds followed by partitioning of those nucleic acids having an increased affinity to the target from the candidate mixture. The partitioned nucleic acids are amplified by PCR and, in an iterative series of selection and amplification steps, enrichment and isolation of specific high affinity aptamers is obtained. See U.S. Pat. No. 5,270,163, describing an in vitro combinatorial method for the identification of nucleic acid ligands.

As used herein, "library" refers to (1) a collection of different individual molecules that have a common generic structure and are produced by combinatorial chemistry, and (2) the products of split combinatorial synthesis of organic molecules having a common core structure or template which has a discrete number of independently variable substituents, each of which can have one of a defined range of values. Combinatorial chemistry involves linking together, in an essentially step-wise fashion, identical or non-identical building blocks such as monomeric subunits, chemical groups, and the like, to form libraries of new compounds. In some aspects, the library is designed to contain significant if not nearly equal representation of all possible different individual molecules that can be theoretically generated given the chemistry and added constituents. In some aspects, the templates may have a number of different functional sites, including those where each site is amenable to a different coupling chemistry and where a plurality of different substituents are introduced for binding to a different site at succeeding coupling steps.

As used herein, "QM1114-DS" refers to a formulation of botulinum neurotoxin type A (BoNT/A, subtype A1) that is stable in liquid form and does not require reconstitution or admixing prior to use.

As used herein, "synthesize" and "synthesized" refers to artificial synthesis, and not merely modifying a naturally occurring sequence.

The present technology is not to be limited in terms of the particular aspects described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

II. Botulinum Neurotoxins (BoNTs) and SNAP25

BoNTs have been traditionally classified into seven serotypes distinguishable with animal antisera and designated with the letters, A, B, C, D, E, F, G, and H. Molecular genetic analysis has led to the discovery of genes encoding for many novel BoNTs, include subtypes within each of the serotypes, expanding the known genus of BoNTs drastically over the last decade. While the first discovered BoNTs were known to be produced by *Clostridium botulinum*, multiple *Clostridium* species produce BoNTs.

Mammalian intoxication with BoNT in vivo leads to flaccid paralysis by blockade of acetylcholine release at neuromuscular junctions. The proteolytic activity of the toxin resides within the 50 kDa light chain domain and is directed against three synaptic proteins, one of which is synaptosomal-associated protein of 25 kDa (SNAP25).

SNAP25 is a t-SNARE protein that is encoded by the SNAP25 gene in humans. SNAREs are soluble N-ethylmaleimide-sensitive factor attachment protein receptors) located on vesicle membranes (v-SNAREs) and target membranes (T-SNAREs). The assembled v-SNARE/t-SNARE complex consists of a bundle of four helices, one of which is supplied by v-SNARE and the other three by t-SNARE. SNAP25 is a component of the trans-SNARE complex and is involved in the molecular regulation of neurotransmitter release. Accordingly, SNAP25 plays an important role in the synaptic function of neuronal systems. BoNTs cleave SNAP25, which prevents regulation of neurotransmitter release, thus accounting for systemic flaccid paralysis.

III. X-Aptamers

X-aptamers are synthetic affinity molecules comprising both naturally occurring and chemically modified nucleic acids that function similarly to antibodies, but are based on an oligonucleotide backbone with or without protein-like sidechains. X-aptamers differ from aptamers in at least two regards, (1) X-aptamers utilize modified bases such as indols, amines, and phenols as well as standard nucleotide bases, and (2) X-aptamers are not created via the standard SELEX methods used to create aptamers. While this disclosure describes aptamers and X-aptamers, X-aptamers are the preferred form.

While utilizing aptamers to bind to proteins and other molecules has been known in the state of the art for some time, their multiple drawbacks are equally well known, particularly their high sensitivity to nuclease digestion that makes them unstable and thus impracticable for many uses. In some aspects, X-aptamers of the present disclosure exhibit enhanced nuclease stability compared to their aptamer counterparts.

X-aptamers function as detection molecules, much like antibodies, but are based on an oligonucleotide backbone with or without protein-like side chains. These X-aptamers are not made by immunization, as antibodies, rather they are produced synthetically. Affinity for specific targets is achieved through an in vitro selection, by "fishing" using targets and gradually increasing the stringency of the selection. Methods of creating X-aptamers and utilizing X-aptamers to bind and identify proteins and other molecules are described in U.S. Pat. No. 9,988,623, In some aspects, the fishing/capture system utilized to identify X-aptamers that bind to target proteins, such as SNAP25 or fragments of SNAP25. The SNAP25 and/or the SNAP25 fragments are synthesized with a biotin group on the end. The biotin labeled protein pieces are bound onto streptavidin coated magnetic beads (i.e., immobilization of the target). Then the cleaned X-aptamer library (cleaned via a negative selection process for strong binders to negative control peptides or fragments thereof) is mixed with the beads in a tube. The tube is placed in a magnetic stand, and the magnetic beads stick to the tube wall. Because the targets (fragments of SNAP25) are immobilized onto the magnetic beads, an X-aptamers that bind the target is also stuck. After this, a series of stringency washes are performed, which will remove all unbound and weakly bound X-aptamers, retaining only strongly bound aptamers. Next, these strongly bound X-aptamers are removed from the beads using a sodium hydroxide buffer, and the mix of binding aptamers are sequenced using next generation sequenced, and those sequences that specifically bound the target can be synthesized.

While antibodies raised to particular antigens have been utilized for years in detecting any number of antigens, there can be a host of variations, both major and minor, between different batches of antibodies that can prove problematic to good manufacturing practices that rely upon the continuity of antibodies from batch to batch to create a product. Furthermore, production of X-aptamers are approximately 100-fold less expensive that antibodies.

The X-aptamers, in some aspects, are produced via a bead-based split synthesis selection process, as described in U.S. Pat. No. 9,988,623. Split synthesis as originally adapted to generation of single bead peptide libraries was developed to generate one-bead one-oligonucleotide libraries where each bead presents many copies of a single oligonucleotide sequence or species. See U.S. Pat. No. 7,388,762.

In some aspects, copies of a single, chemically pure phosphorothioate oligonucleotide (S-ODN) are introduced onto each bead by the 'mix and separate' split synthesis method. Although oligonucleotides are relatively chemically stable, they are particularly susceptible to enzymatic degradation by nucleases. Controlled inclusion of modified residues such as thiophosphate (S-ODN) and dithiophosphate ($S_2$-ODN) residues is able to confer nuclease resistance and improve the binding properties of aptamers. See U.S. Pat. No. 6,423,493.

In some aspects, polystyrene beads with a non-cleavable hexaethyleneglycol linker attaching the first phosphoramidite are used such that the synthesized ODNs are still covalently attached to the beads after full base and phosphate ester deprotection. The X-aptamer oligonucleotide chains described herein will typically have sections that are non-random. In some aspects, the 5' and/or the 3' terminus comprise preselected sequences of PCR primers and may be generated by first nonrandom programmed stepwise addition to supports in one or more of the synthesis chambers. The 5' and 3' primer sequences may have functional roles in the ultimate X-aptamer. For example, the 5' and 3' sequences may be designed to contribute to a resulting stem-loop structure.

In some aspects, the X-aptamer comprises a heterologous sequence or molecule. In some aspects, the X-aptamer comprises an amino acid. In some aspects, the X-aptamer comprises a conjugated heterologous molecule. In some aspects, the conjugated molecule is a protein. In some aspects, the protein is an enzyme. In some aspects, the heterologous molecule is a quantum dot. In some aspects, the heterologous molecule is a fluorescent molecule. In some aspects the fluorescent molecule is a fluorescent protein. In some aspects, the heterologous molecule is a magnetic particle. In some aspects, the conjugated molecule is a dye. In some aspects, the conjugated molecule is a chelator. In some aspects, the conjugated molecule is a chemical linker that further links an additional molecule.

In some aspects, the heterologous sequence or molecule is utilized to purify or isolate the X-aptamer. In some aspects, the heterologous sequence or molecule is utilized to purify or isolate the SNAP25, or fragments thereof, which are bound to the X-aptamer.

In some aspects, methods of producing the X-aptamer utilize a bead-based process. This process avoids the many rounds of solution enrichment and amplification of potential binding agents required by SELEX, and so can be accomplished much faster than SELEX, usually in one or two rounds. This is because each bead of the bead based library contains thousands of copies of the identical sequence and will therefore capture sufficient labeled target to be selectable in the first instance. With SELEX there will not be detectable numbers of copies of a given sequence for many rounds of amplification. Additionally, while the SELEX process is limited to binding agents (aptamers) consisting of nucleic acids that can be generated enzymatically, the bead-based process is not constrained by the type of nucleic acids (normal or chemically modified) used in the starting library.

Where identification of the target selected oligonucleotides is to be conducted by PCR, the only limitation on applicable chemical modifications is whether a chemically modified sequence can be read by the DNA polymerase used in PCR. The location of the modification is determined by comparing the selected sequence with the column program to determine where the modification must be. With the sequence and the modification site in hand, the identified X-aptamer can be synthesized. In contrast, in SELEX, the PCR product must be a faithful copy of the original sequence which is impossible for many modifications because the DNA polymerase will only copy the sequence using unmodified nucleotides—it is unable to build a faithful copy that includes the modifications for the further required iterative rounds.

In some aspects, all possible types of DNA modifications that can be chemically synthesized can be utilized in the X-aptamers, so long as a nucleic acid polymerase can read the sequence. In some aspects, the modifications in the X-aptamers can be either in the backbone, the deoxyribose (and ribose) sugars, or the bases.

In some aspects, backbone modifications that can occur in the X-aptamers include phosphate, monothioate, dithioate, methyl phosphonate, alkyl phosphonate. The thioates provide enhanced nuclease stability and can enhance X-aptamer binding affinity without sacrificing specificity. The dithioates are incompatible with conventional SELEX because they cannot be incorporated into synthesized stands by the polymerase.

In some aspects, modifications to the sugars can occur in the X-aptamers, including (Deoxy)-Ribose-2'-fluoro, 2'-OMe, 2'-methyl, and 2'-deoxy-2'-fluoro-D-arabinose.

In some aspects, base substitutions can occur in the X-aptamers, including 5-(3-aminoallyl)-deoxyuridyl, 5-(alkynyl)-deoxyuridyl, and 3-(2-Deoxy-b-D-ribofuranosyl)-1,3-diaza-2-oxophenothiazine. Many other modifications of base substitutes are possible so long as a nucleic acid polymerase can read the sequence that includes the modification. In some aspects, the various potential base substitutions permit virtually unlimited chemical functionality including addition of positive charges, hydrophobic groups, amino acids, and small molecule drugs. After selection and identification, the base substitutions can be easily incorporated at selected positions, directly during synthesis or post-synthetically using amide coupling or click-chemistry. The present technology provides a means to include these modifications, which are incompatible with techniques such as SELEX that rely on amplification of faithful copies with each round of selection.

In some aspects, high binding affinity partially monothioate DNA aptamers are first selected against a desired target. These aptamers can be selected by methods such as SELEX or from bead-based libraries. It is noted in this context and for purposes of clarification, that SELEX can only be used to select partially monothioate aptamers as used as the starting material. For fully monothioate aptamers as starting materials, a bead-based process would be employed because SELEX cannot be used to prepare fully monothioate aptamers.

In some aspects, in bead-based library selection each bead is constructed to have many copies of the same unique sequence on its surface. After binding to labeled target, beads binding high amounts of the target are selected and isolated from the remaining majority of beads, which bind no or low amounts of the target. Bead selection can be achieved by any suitable method. For example, the target can be rendered fluorescent (by attachment of fluorescent dyes), and beads that bind large amounts of the target can be identified by their high fluorescence relative to other beads. Such beads can be isolated by manual recovery using a micropipettor, by automated fluorescence-activated sorting. The sequences on the selected beads are determined, most typically by PCR combined with sequencing and characterization of the sequence. Where X-groups have been added to the sequences during construction, the location of the X-groups is determined by consulting the program by which the nucleotides were added to the beads. This method has considerable advantages including very high selective enrichment, isolation in a single cycle, no PCR amplification bias and no chemistry limitations, except, in the case of sequence determination by PCR, that the nucleic acid polymerase be able to read the sequence on the bead.

In some aspects, pre-selected aptamers serve as the lead sequences for the design of high-sequence-diversity X-aptamers although it is also possible to incorporate X groups into a random library from the beginning. In some aspects, it is not necessary to start with an existing aptamer sequence and then try to improve it by adding X groups at random positions.

In some aspects, X-aptamers comprise both nuclease resistance and expanded chemical functionalities, specifically drug-like molecules added to 5-positions of certain uridines on a completely monothiophosphate-backbone substituted oligonucleotide aptamer. By combining one-bead, one-sequence thioaptamer selection method with the incorporation of pseudo-randomly placed bases containing chemical linkers, additional X-ligands can be appended onto aptamers or thioaptamers to create a next-generation, X-aptamer library, and the best binding X-aptamers can be selected from this large pool of sequences.

In some aspects, X-aptamers are designed to recognize the native protein structure of human SNAP25, and fragments thereof. In some aspects, the fragments thereof are the fragments created by cleavage of SNAP25 by any one of the BoNTs. The SNAP25 cleavage sites are well-characterized, and the SNAP25 fragments as a result of BoNT cleavage of SNAP25 are a known and defined genus.

In some aspects, the X-aptamer is a synthetic oligonucleotide sequence selected from the group consisting of SEQ ID NOs:1-96. In some aspects, the X-aptamer sequence comprises the W symbol, which corresponds to a modified nucleotide comprising an indol. In some aspects, the X-aptamer sequence comprises the X symbol, which corresponds to a modified nucleotide comprising an amine. In some aspects, the X-aptamer sequence comprises the Y symbol, which corresponds to a modified nucleotide comprising a phenol. In some aspects, the modified nucleotide is a deoxyuridine. In some aspects, the modified nucleotide is a deoxyuridine derivative. In some aspects, the modified nucleotide is a deoxycytidine analog. In some aspects, the modified nucleotide is a phosphoramidite, such as carboxy-dT, TC-CE, tC °-CE, or tCnitro-CE. In some aspects, the modified nucleotide is a dA thiophosphoramidite, a dC thiophosphoramidite, a dG thiophosphoramidite, or a dT thiophosphoramidite. In some aspects, the modified nucleotide is 5-aminoallyl-dU. In some aspects, the modified nucleotide is a 5-[N-(2-aminoethyl)-3-(E)-acrylamido]-2'-deoxyuridine. In some aspects, the modified nucleotide is a 5-(aminoethyl)-3-acrylamido)-deoxyuridine, which is also known as amino-dU. In some aspects, the modified nucleotide is a deoxyribonucleotide triphosphate. In some aspects, the modified nucleotide is instead a modified nucleoside.

In some aspects, the modified nucleotide comprising an indol is a modified nucleic acid comprising the indol group of tryptophan. In some aspects, the modified nucleotide comprising a phenol group is a modified nucleic acid comprising the phenol group of tyrosine.

In some aspects, the oligonucleotide sequences selected from SEQ ID NOs:1-96 comprise one or more X, which represents a modified nucleotide comprising an amine group. In some aspects, the oligonucleotide sequences selected from SEQ ID NOs:1-96 comprise one or more W, which represents a modified nucleotide comprising an indol group. In some aspects, the oligonucleotide sequences selected from SEQ ID NOs:1-96 comprise one or more Y, which represents a modified nucleotide comprising a phenol group.

In some aspects, the Y represents any modified nucleotide comprising a phenol functional group. In some aspects, the X represents any modified nucleotide comprising an amine functional group. In some aspects, the W represents any modified nucleotide comprising an indol functional group.

In some aspects, the X-aptamer is bound to one or more additional molecules. In some aspects, the one or more additional molecules is SNAP25 or a fragment thereof. In some aspects, the SNAP25 fragment is Peptide 1, Peptide 2, Peptide 3, or Peptide 4. In some aspects, the additional molecule is a nucleic acid sequence or an amino acid sequence. In some aspects, the additional molecule is a protein or an enzyme. In some aspects, the additional molecule is a quantum dot, a fluorescent molecule, a fluorescent protein, a dye, or a chelator. In some aspects, the additional molecule is a linker molecule that further links another molecule.

In some aspects, the one or more additional molecules is a ROX fluorophore, a Fam fluorophore, a TAMRA fluorophore, or an Alexa fluorophore. In some aspects, the one or more additional molecules is horseradish peroxidase. In some aspects, the one or more additional molecules is alkaline phosphatase. In some aspects, the one or more additional molecules is an oligonucleotide sequence recognized by one or more antibodies.

In some aspects, the oligonucleotides of SEQ ID NOs:1-96, or any of the oligonucleotides described herein, exhibit affinities to their respective binding partners (detailed in Table 1 and Table 2) with a $K_D$ of between $1\times10^{-6}$ to $1\times10^{-13}$. In some aspects, the aptamers and X-aptamers described herein exhibit affinities to their respective binding partners with a $K_D$ of between $1\times10^{-6}$ to $1\times10^{-13}$, $1\times10^{-6}$ to $1\times10^{-12}$, $1\times10^{-6}$ to $1\times10^{-11}$, $1\times10^{-6}$ to $1\times10^{-10}$, $1\times10^{-6}$ to $1\times10^{-9}$, $1\times10^{-6}$ to $1\times10^{-8}$, $1\times10^{-8}$ to $1\times10^{-13}$, $1\times10^{-8}$ to $1\times10^{-12}$, $1\times10^{-8}$ to $1\times10^{-11}$, $1\times10^{-8}$ to $1\times10^{-10}$, $1\times10^{-8}$ to $1\times10^{-9}$, $1\times10^{-9}$ to $1\times10^{-13}$, $1\times10^{-9}$ to $1\times10^{-12}$, $1\times10^{-9}$ to $1\times10^{-11}$, or $1\times10^{-9}$ to $1\times10^{-10}$. In some aspects, the aptamers and X-aptamers described herein exhibit affinities to their respective binding partners with a $K_D$ of about $1\times10^{-6}$, about $5\times10^{-6}$, about $1\times10^{-7}$, about $5\times10^{-7}$, about $1\times10^{-8}$, about $5\times10^{-8}$, about $1\times10^{-9}$, about $5\times10^{-9}$, about $1\times10^{-10}$, about $5\times10^{-10}$, about $1\times10^{-11}$, about $5\times10^{-11}$, about $1\times10^{-12}$, about $5\times10^{-12}$, about $1\times10^{-13}$, or about $5\times10^{-13}$.

In some aspects, the X-aptamer is in a composition. In some aspects, the composition comprises the X-aptamer selected from the group consisting of SEQ ID NOs:1-96. In some aspects, the composition comprises one or more X-aptamers selected from the group consisting of SEQ ID NOs:1-96. In some aspects, the composition comprises two X-aptamers selected from the group consisting of SEQ ID NOs:1-96. In some aspects, the composition comprises three X-aptamers selected from the group consisting of SEQ ID NOs:1-96.

In some aspects, the X-aptamer is in a kit. In some aspects, the kit comprises the X-aptamer selected from the group consisting of SEQ ID NOs:1-96. In some aspects, the kit comprises one or more X-aptamers selected from the group consisting of SEQ ID NOs:1-96. In some aspects, the kit comprises two X-aptamers selected from the group consisting of SEQ ID NOs:1-96. In some aspects, the kit comprises three or more X-aptamers selected from the group consisting of SEQ ID NOs:1-96.

In some aspects, the X-aptamers of SEQ ID NOs:1-96 are further modified by removing the W, X, and Y nucleotides comprising the indol, amine, and phenol functional groups, thus creating aptamers. In a further aspect, these aptamers are created by replacing the W, X, and Y with any nucleotide. In some aspects, the X-aptamers of SEQ ID NOs:1-96 are further modified to comprise part DNA and part RNA. In some aspects, the X-aptamers of SEQ ID NOs:1-96 are further modified to convert the DNA sequences into RNA sequences, such that In some aspects, the nucleic acid sequences comprise at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one of SEQ ID NOs:1-96. In some aspects, the nucleic acid sequences comprise at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to any one of SEQ ID NOs:1-96.

In some aspects, the nucleic acid sequences comprise about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity to any one of SEQ ID NOs:1-96. In some aspects, the nucleic acid sequences comprise 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs:1-96.

In some aspects, the oligonucleotides of the present disclosure differ by 10 nucleotides from any one of SEQ ID NOs:1-96. In some aspects, the oligonucleotides of the present disclosure differ by about 10 nucleotides from any one of SEQ ID NOs:1-96. In some aspects, the oligonucleotides of the present disclosure differ by 9 nucleotides from any one of SEQ ID NOs:1-96. In some aspects, the oligonucleotides of the present disclosure differ by 8 nucleotides from any one of SEQ ID NOs:1-96. In some aspects, the oligonucleotides of the present disclosure differ by 7 nucleotides from any one of SEQ ID NOs:1-96. In some aspects, the oligonucleotides of the present disclosure differ by 6 nucleotides from any one of SEQ ID NOs:1-96. In some aspects, the oligonucleotides of the present disclosure differ by 5 nucleotides from any one of SEQ ID NOs:1-96. In some aspects, the oligonucleotides of the present disclosure differ by 4 nucleotides from any one of SEQ ID NOs:1-96. In some aspects, the oligonucleotides of the present disclosure differ by 3 nucleotides from any one of SEQ ID NOs:1-96. In some aspects, the oligonucleotides of the present disclosure differ by 2 nucleotides from any one of SEQ ID NOs:1-96. In some aspects, the oligonucleotides of the present disclosure differ by 1 nucleotide from any one of SEQ ID NOs:1-96.

In the context of creating modified versions of SEQ ID NOs:1-96 that are still capable of binding SNAP25 or fragments thereof, one of ordinary skill in the art would avoid modifying the first 7 nucleotides on the 5' end and the last 5 nucleotides on the 3' end of the oligonucleotide. In some aspects, one of ordinary skill in the art would avoid modifying nucleotide position 12, 13, 22, of any one of SEQ ID NOs:1-96.

In some aspects, SEQ ID NOs:1-96 comprise linker sequences which act as binding sites for primers or for ligation sites for ligation an additional oligonucleotide sequence comprising a primer binding site.

In some aspects, one or more X-aptamers are utilized to isolate or purify SNAP25, or a fragment thereof. In some aspects, the method comprises administering a composition comprising SNAP25, or a fragment thereof, to a composition comprising one or more synthetic oligonucleotide sequences selected from the group consisting of SEQ ID NOs:1-96. In some aspects the sequences are immobilized to a surface. In some aspects, the method further comprises washing impurities from the composition comprising the SNAP25, or the fragment thereof, bound to the synthetic oligonucleotide. In some aspects, the method further comprises eluting the SNAP25 or the fragment thereof from the synthetic oligonucleotide sequence.

In some aspects, one or more X-aptamers bind SNAP25, or a fragment thereof. In some aspects, a method of binding SNAP25, or a fragment thereof, to one or more X-aptamers comprises administering a composition comprising one or more synthetic X-aptamers selected from the group consisting of SEQ ID NOs:1-96 to a composition comprising the SNAP25 or the fragment thereof, and wherein the one or more synthetic X-aptamers bind to the SNAP25 or the fragment thereof.

In some aspects, the composition comprising the SNAP25 or the fragment thereof is an in vivo composition, and in vitro composition, or an in situ composition. In some aspects, the composition comprising the SNAP25 or the fragment thereof is a tissue sample, a tissue culture, a cell culture, or a gel.

In some aspects, the X-aptamer is bound to one or more additional molecules. In some aspects, the one or more additional molecules is SNAP25 or a fragment thereof. In some aspects, the SNAP25 fragment is Peptide 1, Peptide 2, Peptide 3, or Peptide 4. In some aspects, the additional molecule is a nucleic acid sequence or an amino acid sequence. In some aspects, the additional molecule is a protein or an enzyme. In some aspects, the additional molecule is a quantum dot, a fluorescent molecule, a fluorescent protein, a dye, or a chelator. In some aspects, the additional molecule is a linker molecule that further links another molecule.

In some aspects, the one or more additional molecules is a ROX fluorophore, a Fam fluorophore, a TAMRA fluorophore, or an Alexa fluorophore. In some aspects, the one or more additional molecules is horseradish peroxidase. In some aspects, the one or more additional molecules is alkaline phosphatase. In some aspects, the one or more additional molecules is an oligonucleotide sequence recognized by one or more antibodies

EXAMPLES

Example 1

SNAP25-Binding X-Aptamers

X-aptamers were designed to recognize the native protein structure of human SNAP25. Four selection peptides (peptides 1-4 described herein) and full length SNAP25 were engineered, FIG. 1, for the selection process.

Peptide 1 and Peptide 2 were used to find X-aptamers capable of binding both full length and cleaved SNAP25. Peptide 3 was designed to raise X-aptamers that recognize uncleaved SNAP25. Peptide 4 was designed to identify the region where SNAP24 is cleaved by BoNT/A, resulting in X-aptamers specific for cleaved SNAP25. The full length SNAP25 utilized in the example had FLAG and MYC tags, so these were added in the selection process as negative targets, to rid the X-aptamer pool of X-aptamers binding to FLAG or MYC.

A total of 96 X-aptamers (Table 1) were found in the screening using Peptides 1-4 (SEQ ID NOs:97-100). Each of Peptides 1, 2, and 4 are subsequences of SNAP25, and a fragment of Peptide 3 is a subsequence of SNAP, as depicted in FIG. 1. Several slightly different X-aptamers were found to bind to each target, described in Table 2. The differences lie in both the oligonucleotide sequence, but also the presence of the following functional groups: indol (W), amine (X), and phenol (Y).

TABLE 1

Total number of X-aptamers with a positive selection for each target.

| X-Aptamer Name | Number of Specific X-aptamers | Target |
|---|---|---|
| SNAP | 8 | Whole SNAP25 |
| PEP1 | 24 | Peptide 1, whole and cleaved SNAP25 |
| PEP2 | 18 | Peptide 2, whole and cleaved SNAP25 |
| PEP3 | 24 | Peptide 3 and whole SNAP25 |
| PEP4 | 22 | Peptide 4, cleaved SNAP25 |

TABLE 2

X-aptamer binding to SNAP25, PEP1, PEP2, PEP3, PEP4, and negative control peptides.

| SEQ ID NO. | Name | SNAP25 | PEP1 | PEP2 | PEP3 | PEP4 | Negative |
|---|---|---|---|---|---|---|---|
| 1 | SNAP.01 | 113 | 48 | 21 | 4 | 14 | 21 |
| 2 | SNAP.02 | 95 | 52 | 5 | 5 | 18 | 45 |
| 3 | SNAP.03 | 92 | 40 | 19 | 5 | 14 | 21 |
| 4 | SNAP.04 | 83 | 16 | 17 | 5 | 15 | 17 |
| 5 | SNAP.05 | 75 | 44 | 50 | 18 | 35 | 44 |
| 6 | SNAP.06 | 45 | 16 | 4 | 0 | 9 | 19 |
| 7 | SNAP.07 | 38 | 8 | 6 | 3 | 10 | 5 |
| 8 | SNAP.08 | 35 | 8 | 8 | 0 | 4 | 11 |
| 9 | PEP 1.01 | 113 | 2241 | 129 | 205 | 970 | 248 |
| 10 | PEP 1.02 | 16 | 742 | 19 | 4 | 27 | 15 |
| 11 | PEP 1.03 | 93 | 677 | 106 | 54 | 116 | 260 |
| 12 | PEP 1.04 | 5 | 645 | 10 | 0 | 11 | 4 |
| 13 | PEP 1.05 | 89 | 641 | 110 | 29 | 156 | 252 |
| 14 | PEP 1.06 | 17 | 477 | 25 | 8 | 2 | 33 |
| 15 | PEP 1.07 | 141 | 429 | 138 | 49 | 169 | 173 |
| 16 | PEP 1.08 | 30 | 357 | 39 | 15 | 30 | 55 |
| 17 | PEP 1.09 | 33 | 337 | 41 1 | 11 | 33 | 28 |
| 18 | PEP 1.10 | 53 | 293 | 57 | 19 | 47 | 42 |
| 19 | PEP 1.11 | 4 | 293 | 9 | 8 | 11 | 11 |
| 20 | PEP 1.12 | 61 | 289 | 84 | 35 | 73 | 75 |
| 21 | PEP 1.13 | 38 | 27 | 61 | 15 | 68 | 40 |
| 22 | PEP 1.14 | 2 | 241 | 5 | 0 | 3 | 5 |
| 23 | PEP 1.15 | 25 | 220 | 40 | 18 | 37 | 41 |
| 24 | PEP 1.16 | 23 | 212 | 19 | 8 | 30 | 94 |
| 25 | PEP 1.17 | 30 | 200 | 32 | 14 | 23 | 73 |
| 26 | PEP 1.18 | 20 | 200 | 8 | 11 | 39 | 84 |
| 27 | PEP 1.19 | 0 | 200 | 0 | 0 | 3 | 3 |
| 28 | PEP 1.20 | 13 | 188 | 35 | 15 | 61 | 88 |
| 29 | PEP 1.21 | 11 | 188 | 13 | 5 | 8 | 17 |
| 30 | PEP 1.22 | 8 | 184 | 0 | 4 | 6 | 2 |
| 31 | PEP 1.23 | 0 | 168 | 0 | 54 | 0 | 0 |
| 32 | PEP 1.24 | 8 | 160 | 6 | 3 | 15 | 9 |
| 33 | PEP 2.01 | 55 | 44 | 592 | 27 | 51 | 204 |
| 34 | PEP 2.02 | 60 | 56 | 394 | 27 | 55 | 55 |
| 35 | PEP 2.03 | 27 | 68 | 221 | 11 | 46 | 50 |
| 36 | PEP 2.04 | 16 | 44 | 190 | 6 | 44 | 29 |
| 37 | PEP 2.05 | 26 | 44 | 159 | 9 | 24 | 19 |
| 38 | PEP 2.06 | 16 | 36 | 102 | 4 | 15 | 13 |
| 39 | PEP 2.07 | 8 | 32 | 65 | 0 | 14 | 17 |
| 40 | PEP 2.08 | 8 | 20 | 65 | 4 | 13 | 9 |
| 41 | PEP 2.09 | 9 | 20 | 46 | 0 | 6 | 5 |
| 42 | PEP 2.10 | 7 | 0 | 43 | 3 | 8 | 2 |
| 43 | PEP 2.11 | 0 | 0 | 40 | 0 | 3 | 2 |
| 44 | PEP 2.12 | 16 | 12 | 37 | 4 | 21 | 22 |
| 45 | PEP 2.13 | 0 | 24 | 36 | 3 | 6 | 11 |
| 46 | PEP 2.14 | 2 | 20 | 36 | 0 | 4 | 7 |
| 47 | PEP 2.15 | 0 | 0 | 36 | 0 | 8 | 9 |
| 48 | PEP 2.16 | 4 | 20 | 31 | 0 | 5 | 5 |
| 49 | PEP 2.17 | 2 | 0 | 30 | 0 | 2 | 12 |
| 50 | PEP 2.18 | 0 | 8 | 26 | 0 | 3 | 9 |
| 51 | PEP 3.01 | 54 | 245 | 79 | 503 | 69 | 81 |
| 52 | PEP 3.02 | 39 | 329 | 61 | 406 | 50 | 59 |
| 53 | PEP 3.03 | 36 | 120 | 58 | 338 | 71 | 48 |
| 54 | PEP 3.04 | 43 | 44 | 50 | 276 | 50 | 34 |
| 55 | PEP 3.05 | 30 | 44 | 36 | 272 | 42 | 83 |
| 56 | PEP 3.06 | 35 | 120 | 30 | 230 | 37 | 31 |
| 57 | PEP 3.07 | 10 | 144 | 17 | 219 | 38 | 64 |
| 58 | PEP 3.08 | 34 | 84 | 28 | 207 | 28 | 37 |
| 59 | PEP 3.09 | 168 | 64 | 23 | 196 | 25 | 56 |
| 60 | PEP 3.10 | 10 | 48 | 12 | 139 | 25 | 51 |
| 61 | PEP 3.11 | 34 | 8 | 30 | 137 | 24 | 12 |
| 62 | PEP 3.12 | 14 | 44 | 5 | 118 | 19 | 40 |
| 63 | PEP 3.13 | 16 | 16 | 22 | 115 | 18 | 21 |
| 64 | PEP 3.14 | 8 | 36 | 10 | 114 | 14 | 52 |
| 65 | PEP 3.15 | 9 | 56 | 3 | 114 | 26 | 39 |
| 66 | PEP 3.16 | 13 | 0 | 28 | 111 | 24 | 9 |
| 67 | PEP 3.17 | 17 | 40 | 14 | 110 | 17 | 22 |

TABLE 2-continued

X-aptamer binding to SNAP25, PEP1, PEP2,
PEP3, PEP4, and negative control peptides.

| SEQ ID NO. | Name | SNAP25 | PEP1 | PEP2 | PEP3 | PEP4 | Negative |
|---|---|---|---|---|---|---|---|
| 68 | PEP 3.18 | 11 | 72 | 4 | 105 | 16 | 29 |
| 69 | PEP 3.19 | 13 | 12 | 22 | 102 | 14 | 13 |
| 70 | PEP 3.20 | 23 | 8 | 10 | 97 | 15 | 21 |
| 71 | PEP 3.21 | 16 | 12 | 19 | 96 | 18 | 13 |
| 72 | PEP 3.22 | 7 | 44 | 4 | 96 | 22 | 26 |
| 73 | PEP 3.23 | 5 | 56 | 4 | 95 | 13 | 35 |
| 74 | PEP 3.24 | 5 | 56 | 9 | 81 | 12 | 22 |
| 75 | PEP 4.01 | 87 | 216 | 92 | 29 | 257 | 84 |
| 76 | PEP 4.02 | 53 | 40 | 58 | 19 | 208 | 38 |
| 77 | PEP 4.03 | 24 | 64 | 41 | 8 | 202 | 32 |
| 78 | PEP 4.04 | 37 | 64 | 30 | 20 | 186 | 46 |
| 79 | PEP 4.05 | 80 | 140 | 102 | 29 | 170 | 82 |
| 80 | PEP 4.06 | 25 | 28 | 50 | 0 | 131 | 18 |
| 81 | PEP 4.07 | 22 | 44 | 25 | 5 | 105 | 25 |
| 82 | PEP 4.08 | 9 | 20 | 8 | 0 | 94 | 5 |
| 83 | PEP 4.09 | 0 | 0 | 0 | 0 | 85 | 0 |
| 84 | PEP 4.10 | 4 | 72 | 4 | 3 | 76 | 28 |
| 85 | PEP 4.11 | 0 | 0 | 0 | 0 | 67 | 0 |
| 86 | PEP 4.12 | 0 | 0 | 8 | 0 | 61 | 3 |
| 87 | PEP 4.13 | 0 | 0 | 0 | 0 | 57 | 0 |
| 88 | PEP 4.14 | 2 | 44 | 13 | 3 | 37 | 15 |
| 89 | PEP 4.15 | 4 | 72 | 4 | 6 | 37 | 7 |
| 90 | PEP 4.16 | 15 | 8 | 6 | 5 | 35 | 5 |
| 91 | PEP 4.17 | 0 | 0 | 4 | 0 | 24 | 0 |
| 92 | PEP 4.18 | 10 | 12 | 9 | 6 | 18 | 4 |
| 93 | PEP 4.19 | 0 | 12 | 8 | 3 | 18 | 0 |
| 94 | PEP 4.20 | 4 | 0 | 5 | 0 | 18 | 3 |
| 95 | PEP 4.21 | 0 | 0 | 3 | 3 | 18 | 8 |
| 96 | PEP 4.22 | 5 | 8 | 6 | 3 | 17 | 3 |

The data in Table 2 was collected by running direct ELISA assays on the 96 X-aptamers, elucidating their ability to bind SNAP25, SNAP25 fragments (PEP1, PEP2, PEP3, and PEP4), and a negative control. The X-aptamers were biotinylated and immobilized onto streptavidin-coated plates and were utilized as detection molecules. Higher numbers represent strong binding. The negative control peptide is a random peptide to measure the amount of binding that occurs to a random amino acid sequence.

In addition to the initial selection and screening using the peptides, the X-aptamers were tested using biological samples to ensure proper binding to the intended targets and low affinity to other proteins present in protein samples from cell cultures. This was done using both wild type (wt) human embryonic kidney (HEK) cells (which express no or very low levels of SNAP25) and modified HEK cells designed to overexpress SNAP25.

A sandwich ELISA was set up using different X-aptamers as capture molecules, protein samples from wt HEK cells (with no or little SNAP25), and SNAP25 overexpressing HEK cells. A SNAP25 specific antibody (S9684, Sigma-Aldrich) was utilized as the detection molecule. XAs can be used together with other XAs, or as in this assay, together with traditional antibodies.

Fluorescent signals from the sandwich ELISA, FIG. 2, reveal high specific binding to SNAP25 and low binding to other cellular proteins.

Figure 3A:
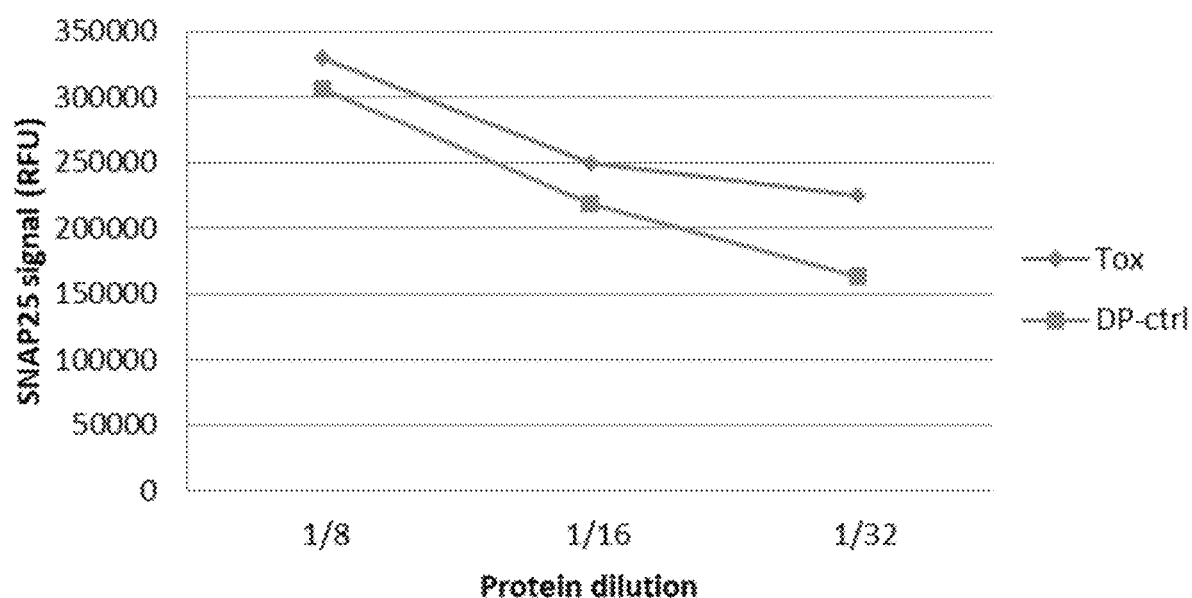
FIG. 3 depicts sandwich ELISAs made using X-aptamers PEP4.04 (FIG. 3A) and PEP4.10 (FIG. 3B) raised against Peptide 4, creating an X-aptamer more specific to BoNT/A-cleaved SNAP25. Protein samples from motor neurons treated with QM1114-DS were used (diamond-pattern line), and a higher binding affinity was seen compared to control samples (square-pattern line) made from protein samples of motor neurons treated only with buffer.
Figure 3B:
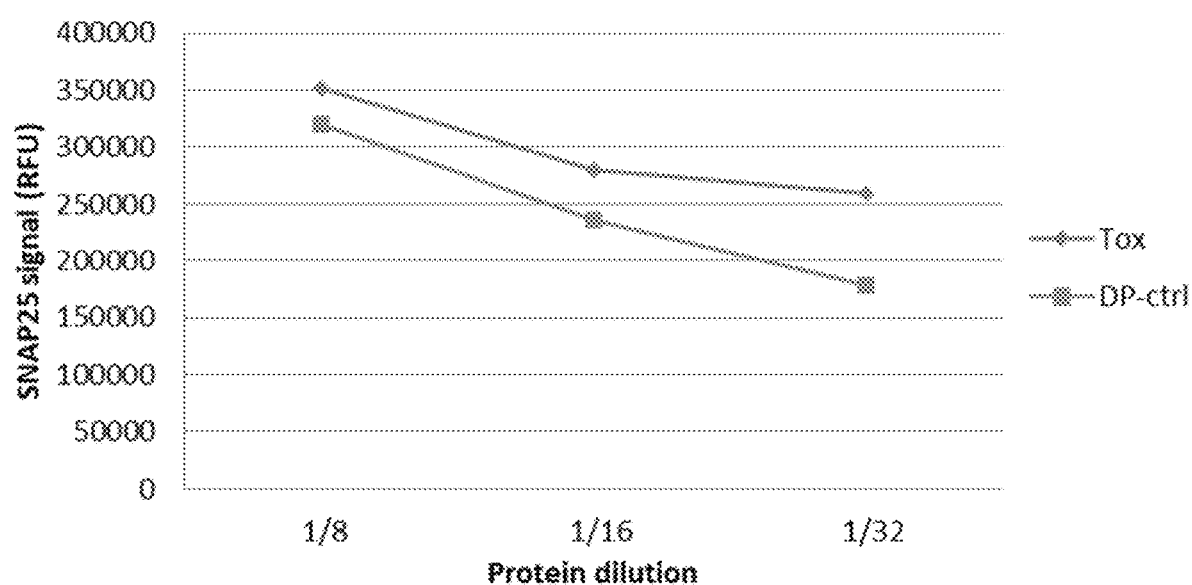

The PEP4 X-aptamers, which were created for only recognizing BoNT/A-cleaved SNAP25 were screened using QM1114-DS-treated motor neuron protein extractions. See FIG. 3A and FIG. 3B.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the disclosure claimed. Thus, it should be understood that although the present disclosure has been specifically disclosed by preferred embodiments and optional features, modification and variation of the disclosure embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein. The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

One skilled in the art readily appreciates that the present disclosure is well adapted to carry out the objects and obtain the ends and advantages mentioned, as well as those inherent therein. Modifications therein and other uses will occur to those skilled in the art. These modifications are encompassed within the spirit of the disclosure and are defined by the scope of the claims, which set forth non-limiting embodiments of the disclosure.

In addition, where features or aspects of the disclosure are described in terms of Markush groups, those skilled in the art will recognize that the disclosure is also thereby described in terms of any individual member or subgroup of members of the Markush group.

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed:

1. A synthetic oligonucleotide sequence selected from the group consisting of SEQ ID NOs:1-96.

2. The oligonucleotide sequence according to claim 1, wherein a modified nucleotide (n) in the synthetic oligonucleotide sequence is a deoxyuridine.

3. The oligonucleotide sequence according to claim 1, wherein a modified nucleotide (n) in the synthetic oligonucleotide sequence is a deoxyribonucleotide triphosphate.

4. The oligonucleotide sequence according to claim 1, wherein the synthetic oligonucleotide is bound to an additional molecule.

5. The oligonucleotide sequence according to claim 4, wherein the additional molecule is selected from the group consisting of SNAP25 or a fragment thereof, a nucleic acid sequence, an amino acid sequence, a protein, an enzyme, a quantum dot, a fluorescent molecule, a dye, a chelator, a magnetic particle, and a linker capable of linking to another molecule.

6. The oligonucleotide sequence according to claim 5, wherein the fluorescent molecule is a fluorescent protein.

7. A composition comprising a synthetic oligonucleotide sequence selected from the group consisting of SEQ ID NOs:1-96.

8. A kit comprising a synthetic oligonucleotide sequence selected from the group consisting of SEQ ID NOs:1-96.

9. A method of isolating SNAP25, or a fragment thereof, the method comprising:
    (a) administering a composition comprising SNAP25, or a fragment thereof, to a composition comprising one or more synthetic oligonucleotide sequences selected from the group consisting of SEQ ID NOs:1-96, wherein the synthetic oligonucleotide sequences are immobilized;
    (b) washing impurities from the SNAP25 or the fragment thereof bound to the immobilized synthetic oligonucleotide; and
    (c) eluting the SNAP25 or the fragment thereof from the immobilized synthetic oligonucleotide sequences.

10. A method of binding SNAP25, or a fragment thereof, with one or more X-aptamers, the method comprising administering a composition comprising one or more synthetic X-aptamers selected from the group consisting of SEQ ID NOs:1-96 to a composition comprising the SNAP25 or the fragment thereof, and wherein the one or more synthetic X-aptamers bind to the SNAP25 or the fragment thereof.

11. The method according to claim 10, wherein the composition comprising the SNAP25 or the fragment thereof is a composition in vivo.

12. The method according to claim 10, wherein the composition comprising the SNAP25 or the fragment thereof is a composition in vitro.

13. The method according claim 10, wherein the composition comprising the SNAP25 or the fragment thereof is a composition in situ.

14. The method according to claim 10, wherein the composition comprising the SNAP25 or the fragment thereof is a tissue sample.

15. The method according claim 10, wherein the composition comprising the SNAP25 or the fragment thereof is a tissue culture.

16. The method according claim 10, wherein the composition comprising the SNAP25 or the fragment thereof is a cell culture.

17. The method according claim 10, wherein the composition comprising the SNAP25 or the fragment thereof is a gel.

18. The method according claim 10, wherein the one or more X-aptamers are bound to an additional molecule.

19. The method according claim 18, wherein the additional molecule is selected from the group consisting of a nucleic acid sequence, an amino acid sequence, a protein, an enzyme, a quantum dot, a fluorescent molecule, a fluorescent protein, a dye, a chelator, a magnetic particle, and a linker capable of linking to another molecule.

* * * * *

SEQUENCE LISTING

<160> NUMBER OF SEQ ID NOS: 103

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer SNAP.01 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group

<400> SEQUENCE: 1
tttttaacac gacncancng tgggncncga acancgangg agtgggccca tg          52

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer SNAP.02 sequence
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 2
tttttaagcc cacacngcng tgaaggacac agcccgacan cgncgngcca tg          52

<210> SEQ ID NO 3
<211> LENGTH: 52

```
<212> TYPE: DNA
<213> ORGANISM: Artificial Sequence
<220> FEATURE:
<223> OTHER INFORMATION: Description of Artificial Sequence: Synthetic
      X-aptamer SNAP.03 sequence
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (36)..(36)
<223> OTHER INFORMATION: a, c, t, or g with an indol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 3
tttttaagcc cacgggngnn cgacagacac agcaanacan cgtgggccca tg            52

<210> SEQ ID NO 4
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer SNAP.04 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group

<400> SEQUENCE: 4
tttttaagcc cacccaccng tggacancga accncacngc agtgggccca tg            52

<210> SEQ ID NO 5
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer SNAP.05 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group

<400> SEQUENCE: 5
tttttaagcc caccccggnn cgccagacga accccaacag tgtgggccca tg            52
```

```
<210> SEQ ID NO 6
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer SNAP.06 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 6
tttttaagcc cacnncgcng tgagcaacga acancgagca ggncgngcca tg           52

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer SNAP.07 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 7
tttttaacac gaccgggcng tgcacancga acacngcggn cgncgngcca tg           52

<210> SEQ ID NO 8
<211> LENGTH: 52
<212> TYPE: DNA
```

<213> ORGANISM: Artificial Sequence
<220> FEATURE:
<223> OTHER INFORMATION: Description of Artificial Sequence: Synthetic
      X-aptamer SNAP.08 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 8
tttttaacac gacngaagnn cgccaggcga acancgtggn ggncgngcca tg            52

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.01 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (35)..(35)
<223> OTHER INFORMATION: a, c, t, or g with a phenol functional group

<400> SEQUENCE: 9
tttttaacac gacgcgacng tgagaggcac agtnnggggg cgtgggccca tg            52

<210> SEQ ID NO 10
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.02 sequence
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:

```
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (36)..(36)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 10
tttttaacac gaccanccng tgccncacga actcantgcc cgncgngcca tg          52

<210> SEQ ID NO 11
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.03 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (36)..(36)
<223> OTHER INFORMATION: a, c, t, or g with an indol functional group

<400> SEQUENCE: 11
tttttaacac gacgggggnn cgggcagcga acagangggc ggtgggccca tg          52

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.04 sequence
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 12
```
tttttaacac gacgcnccng tgacagccga acancatngg tgncgngcca tg          52

<210> SEQ ID NO 13
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.05 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 13
tttttaagcc caccaagcng tggcgggcac agggcagcan cgncgngcca tg          52

<210> SEQ ID NO 14
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.06 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (38)..(38)
<223> OTHER INFORMATION: a, c, t, or g with an indol functional group

<400> SEQUENCE: 14
tttttaagcc caccncagnn cgcncancga acgacgangc tgtgggccca tg          52

<210> SEQ ID NO 15
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.07 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 15
tttttaacac gacncaacng tganncccac agacngggcn cgtgggccca tg            52

<210> SEQ ID NO 16
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.08 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 16
tttttaacac gaccccggnn cgacncccac agagcggggg tgncgngcca tg            52

<210> SEQ ID NO 17
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.09 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (17)..(17)

<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (23)..(23)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group

<400> SEQUENCE: 17
tttttaacac gacnnancng tgncagncga acgncgcgga ggtgggccca tg          52

<210> SEQ ID NO 18
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.10 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (38)..(38)
<223> OTHER INFORMATION: a, c, t, or g with an indol functional group

<400> SEQUENCE: 18
tttttaacac gacgggcgnn cgcnggncga acaccaangc tgtgggccca tg          52

<210> SEQ ID NO 19
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.11 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group

```
<220> FEATURE:
<221> NAME/KEY: modified_base
<222> LOCATION: (36)..(36)
<223> OTHER INFORMATION: a, c, t, or g with an indol functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 19
tttttaacac gacgccagnn cgaaggncac agtnantngg cgncgngcca tg            52

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.12 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 20
tttttaagcc cacaaaagnn cgancagcac aggncgccaa agncgngcca tg            52

<210> SEQ ID NO 21
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.13 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (23)..(23)
<223> OTHER INFORMATION: a, c, t, or g with an indol functional group
<220> FEATURE:
<221> NAME/KEY: modified_base
<222> LOCATION: (25)..(25)
<223> OTHER INFORMATION: a, c, t, or g with an amine functional group
<220> FEATURE:
```

```
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group

<400> SEQUENCE: 21
tttttaagcc caccaaccng tgncncgcga acganggngc cgtgggccca tg            52

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.14 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 22
tttttaagcc caccngacng tggngggcac agtncgccan cgtgggccca tg            52

<210> SEQ ID NO 23
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.15 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (36)..(36)
<223> OTHER INFORMATION: a, c, t, or g with an indol functional group

<400> SEQUENCE: 23
tttttaagcc caccncncng tgggagacac agtnantgca ggtgggccca tg            52
```

```
<210> SEQ ID NO 24
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.16 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (36)..(36)
<223> OTHER INFORMATION: a, c, t, or g with an indol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 24
tttttaacac gacgggccng tgaacaccga actgangggn cgtgggccca tg            52

<210> SEQ ID NO 25
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.17 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 25
tttttaacac gacggcggnn cgccncccga acgnngtngg agncgngcca tg            52

<210> SEQ ID NO 26
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.18 sequence
<220> FEATURE:
<221> NAME/KEY: modified_base
```

```
<222> LOCATION: (19)..(19)
<223> OTHER INFORMATION: a, c, t, or g with a phenol functional group

<400> SEQUENCE: 26
tttttaacac gaccacccng tgcaaggcga actccgtcaa agtgggccca tg              52

<210> SEQ ID NO 27
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.19 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 27
tttttaacac gacanagcng tgacaggcac aggncatggg agncgngcca tg              52

<210> SEQ ID NO 28
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.20 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group

<400> SEQUENCE: 28
tttttaacac gacgaaccng tgcncaacac agaacatcac agtgggccca tg              52

<210> SEQ ID NO 29
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.21 sequence
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
```

```
<222> LOCATION: (24)..(24)
<223> OTHER INFORMATION: a, c, t, or g with an indol functional group
<220> FEATURE:
<221> NAME/KEY: modified_base
<222> LOCATION: (25)..(25)
<223> OTHER INFORMATION: a, c, t, or g with an amine functional group

<400> SEQUENCE: 29
tttttaagcc caccggncng tggnncccac agtgcatgcg agtgggccca tg            52

<210> SEQ ID NO 30
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.22 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group

<400> SEQUENCE: 30
tttttaacac gacnngggnn cggaaggcga accgcagcaa tgtgggccca tg            52

<210> SEQ ID NO 31
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.23 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 31
```
tttttaagcc cacnncacng tggcncgcac aggccgangg ggncgngcca tg        52

<210> SEQ ID NO 32
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 1.24 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (36)..(36)
<223> OTHER INFORMATION: a, c, t, or g with an indol functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 32
tttttaacac gaccgcccng tgggcaacac agggancngc agncgngcca tg        52

<210> SEQ ID NO 33
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.01 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 33
tttttaacac gacgnnacng tggncaccac aggangagcc tgncgngcca tg        52

<210> SEQ ID NO 34
<211> LENGTH: 52

```
<212> TYPE: DNA
<213> ORGANISM: Artificial Sequence
<220> FEATURE:
<223> OTHER INFORMATION: Description of Artificial Sequence: Synthetic
      X-aptamer PEP 2.02 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 34
tttttaagcc cacanacgnn cganggncac agannggcca agncgngcca tg            52

<210> SEQ ID NO 35
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.03 sequence
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group
```

-continued

<400> SEQUENCE: 35
tttttaacac gacggngcng tgcnggncac agcacgcgcg cgncgngcca tg    52

<210> SEQ ID NO 36
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.04 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 36
tttttaacac gacanggcng tggncancac agcgcaccan tgncgngcca tg    52

<210> SEQ ID NO 37
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.05 sequence
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 37
tttttaagcc cacccnacng tggncaccac agtgcaagcc cgncgngcca tg    52

```
<210> SEQ ID NO 38
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.06 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 38
tttttaacac gaccggccng tggncagcac agacngtngn ggncgngcca tg            52

<210> SEQ ID NO 39
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.07 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (36)..(36)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 39
tttttaacac gacgncgcng tggncaacga acaganacaa cgncgngcca tg            52

<210> SEQ ID NO 40
```

<211> LENGTH: 52
<212> TYPE: DNA
<213> ORGANISM: Artificial Sequence
<220> FEATURE:
<223> OTHER INFORMATION: Description of Artificial Sequence: Synthetic
    X-aptamer PEP 2.08 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 40
tttttaagcc cacgnnngnn cggnggncac agcacgccac ggncgngcca tg           52

<210> SEQ ID NO 41
<211> LENGTH: 52
<212> TYPE: DNA
<213> ORGANISM: Artificial Sequence
<220> FEATURE:
<223> OTHER INFORMATION: Description of Artificial Sequence: Synthetic
    X-aptamer PEP 2.09 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (35)..(35)
<223> OTHER INFORMATION: a, c, t, or g with a phenol functional group

```
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 41
tttttaacac gacanaggnn cgcnggncac agaangtngn ggtgggccca tg          52

<210> SEQ ID NO 42
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.10 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 42
tttttaagcc cacnggccng tggncagcga actgngcgcn ggtgggccca tg          52

<210> SEQ ID NO 43
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.11 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (27)..(27)
<223> OTHER INFORMATION: a, c, t, or g with an amine functional group

<400> SEQUENCE: 43
tttttaagcc cacnnggcng tgcacancac agaacaagca ggtgggccca tg          52

<210> SEQ ID NO 44
<211> LENGTH: 52
<212> TYPE: DNA
```

```
<213> ORGANISM: Artificial Sequence
<220> FEATURE:
<223> OTHER INFORMATION: Description of Artificial Sequence: Synthetic
      X-aptamer PEP 2.12 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (23)..(23)
<223> OTHER INFORMATION: a, c, t, or g with an indol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 44
tttttaacac gacnagacng tgnacccac agggcaangn ggncgngcca tg          52

<210> SEQ ID NO 45
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.13 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
```

<222> LOCATION: (46)..(46)
<223> OTHER INFORMATION: a, c, t, or g with a phenol functional group

<400> SEQUENCE: 45
tttttaagcc cacangccng tggncancga acannggggcc ggncgngcca tg    52

<210> SEQ ID NO 46
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.14 sequence
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group

<400> SEQUENCE: 46
tttttaagcc cacgggncng tggncaccga acgacgtggc agtgggccca tg    52

<210> SEQ ID NO 47
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.15 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 47
tttttaacac gacgnnacng tggncaccac aggangagcn tgncgngcca tg    52

<210> SEQ ID NO 48

```
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.16 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group

<400> SEQUENCE: 48
tttttaagcc cacanaggnn cggnggncac agtgnggngc ggtgggccca tg            52

<210> SEQ ID NO 49
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.17 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 49
tttttaacac gacgnnacng tggncaccac aggangaggc tgncgngcca tg            52
```

<210> SEQ ID NO 50
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 2.18 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 50
tttttaacac gacgnnacng tggncancac aggangagcc tgncgngcca tg            52

<210> SEQ ID NO 51
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.01 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (36)..(36)
<223> OTHER INFORMATION: a, c, t, or g with an indol functional group
<220> FEATURE:

<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 51 ttttaacac gacaccacng tggnncncac agcnangngn tgtgggccca tg          52

<210> SEQ ID NO 52
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.02 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 52 ttttaacac gacagcacng tggnncgcga accncaagcn cgncgngcca tg          52

<210> SEQ ID NO 53
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.03 sequence
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base

```
<222> LOCATION: (38)..(38)
<223> OTHER INFORMATION: a, c, t, or g with an indol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 53
tttttaacac gacaanggnn cgggggggcga acgncacngn ggncgngcca tg          52

<210> SEQ ID NO 54
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.04 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 54
tttttaagcc cacggcacng tgcncagcac agcncggggn ggtgggccca tg          52

<210> SEQ ID NO 55
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.05 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (23)..(23)
<223> OTHER INFORMATION: a, c, t, or g with an indol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (38)..(38)
<223> OTHER INFORMATION: a, c, t, or g with an indol functional group

<400> SEQUENCE: 55
tttttaacac gacgacacng tgnngggcga actccgcngg ggtgggccca tg          52

<210> SEQ ID NO 56
```

```
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.06 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 56
tttttaacac gaccgcacng tganaggcga acggngtgga ggncgngcca tg            52

<210> SEQ ID NO 57
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.07 sequence
<220> FEATURE:
<221> NAME/KEY: modified_base
<222> LOCATION: (19)..(19)
<223> OTHER INFORMATION: a, c, t, or g with a phenol functional group

<400> SEQUENCE: 57
tttttaagcc cacgacacng tggccaacac agtacatgca tgtgggccca tg            52

<210> SEQ ID NO 58
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.08 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (40)..(40)
```

```
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 58 ttttttaacac gacgncacng tggnncncga acgccgcgcn tgncgngcca tg        52

<210> SEQ ID NO 59
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.09 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (23)..(23)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group

<400> SEQUENCE: 59 ttttttaagcc cacngcacng tgnacancga actgcaccaa cgtgggccca tg        52

<210> SEQ ID NO 60
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.10 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group

<400> SEQUENCE: 60 ttttttaacac gacagcacng tgcacagcac agcncaaggg tgtgggccca tg        52

<210> SEQ ID NO 61
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.11 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (16)..(16)
```

<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 61
tttttaagcc cacngncgnn cggcgggcga acgacagcan ggncgngcca tg            52

<210> SEQ ID NO 62
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.12 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group

<400> SEQUENCE: 62
tttttaacac gacnanccng tgagcaacac agggcggcac tgtgggccca tg            52

<210> SEQ ID NO 63
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.13 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 63
tttttaacac gacancacng tgcacagcga actgcgtngg cgncgngcca tg              52

<210> SEQ ID NO 64
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.14 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group

<400> SEQUENCE: 64
tttttaacac gacaccacng tgcccaccac agtncacnga agtgggccca tg              52

<210> SEQ ID NO 65
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.15 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (36)..(36)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 65
tttttaacac gacngcacng tgaancncga acgcancggg agncgngcca tg              52

<210> SEQ ID NO 66
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.16 sequence

```
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group

<400> SEQUENCE: 66
tttttaagcc cacancacng tgcgagccac agancaggca ggtgggccca tg            52

<210> SEQ ID NO 67
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.17 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (27)..(27)
<223> OTHER INFORMATION: a, c, t, or g with an amine functional group

<400> SEQUENCE: 67
tttttaagcc cacnagagnn cggccancac agtccaacac tgtgggccca tg            52

<210> SEQ ID NO 68
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.18 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (36)..(36)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group
```

<400> SEQUENCE: 68
tttttaacac gacacgggnn cgcacancac agaganacac tgncgngcca tg            52

<210> SEQ ID NO 69
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.19 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 69
tttttaagcc cacgccacng tgaccancga accacacggc cgncgngcca tg            52

<210> SEQ ID NO 70
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.20 sequence
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (23)..(23)
<223> OTHER INFORMATION: a, c, t, or g with an indol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group

<400> SEQUENCE: 70
tttttaagcc cacagnncng tgnncancac agagcaacac tgtgggccca tg            52

<210> SEQ ID NO 71
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.21 sequence
<220> FEATURE:

```
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (23)..(23)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 71
tttttaagcc cacnccggnn cgnccancac agcccacngn ggncgngcca tg            52

<210> SEQ ID NO 72
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.22 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 72
tttttaacac gacancacng tggaagacac aggacgtgcg tgncgngcca tg            52

<210> SEQ ID NO 73
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.23 sequence
<220> FEATURE:
<221> NAME/KEY: modified_base
```

```
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group

<400> SEQUENCE: 73
tttttaagcc caccncacng tgcaagncac aggncggcac cgtgggccca tg            52

<210> SEQ ID NO 74
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 3.24 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 74
tttttaagcc caccagggnn cgggagccga acgccagcac tgncgngcca tg            52

<210> SEQ ID NO 75
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.01 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (38)..(38)
```

<223> OTHER INFORMATION: a, c, t, or g with an indol functional group

<400> SEQUENCE: 75
tttttaagcc cacaagcgnn cggcncncac agancgtnga cgtgggccca tg    52

<210> SEQ ID NO 76
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.02 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group

<400> SEQUENCE: 76
tttttaagcc cacnacngnn cgaagggcac agtccaggcc ggtgggccca tg    52

<210> SEQ ID NO 77
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.03 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (23)..(23)
<223> OTHER INFORMATION: a, c, t, or g with an indol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 77
tttttaacac gacaggggnn cgnaggacac aggnngangn tgtgggccca tg    52

<210> SEQ ID NO 78
<211> LENGTH: 52

```
<212> TYPE: DNA
<213> ORGANISM: Artificial Sequence
<220> FEATURE:
<223> OTHER INFORMATION: Description of Artificial Sequence: Synthetic
      X-aptamer PEP 4.04 sequence
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 78
tttttaagcc cacganccng tgcnncgcac agcncgagcn agtgggccca tg            52

<210> SEQ ID NO 79
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.05 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (36)..(36)
<223> OTHER INFORMATION: a, c, t, or g with an indol functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 79
tttttaagcc cacanaagnn cgcaagncac agcgangnga tgncgngcca tg            52
```

-continued

```
<210> SEQ ID NO 80
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.06 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 80
tttttaagcc cacgagagnn cganagncac agannggcac cgncgngcca tg          52

<210> SEQ ID NO 81
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.07 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 81
tttttaagcc cacncgngnn cgcacaccga accacaagcn agtgggccca tg          52
```

```
<210> SEQ ID NO 82
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.08 sequence
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group

<400> SEQUENCE: 82
tttttaacac gaccanncng tgccagccga actccgtgcn ggtgggccca tg            52

<210> SEQ ID NO 83
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.09 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 83
tttttaacac gacanangnn cgacggacac agtgngtggc ggncgngcca tg            52

<210> SEQ ID NO 84
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.10 sequence
<220> FEATURE:
<221> NAME/KEY: modified_base
```

```
<222> LOCATION: (19)..(19)
<223> OTHER INFORMATION: a, c, t, or g with a phenol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (40)..(40)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 84
tttttaagcc cacaagacng tgcgncgcac agannggcan cgncgngcca tg            52

<210> SEQ ID NO 85
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.11 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (23)..(23)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 85
tttttaagcc cacccgagnn cgnccagcga accacgcgcg tgncgngcca tg            52

<210> SEQ ID NO 86
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.12 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (38)..(38)
```

<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 86
tttttaacac gacagcccng tgcaggccga acggcgtnga tgncgngcca tg                52

<210> SEQ ID NO 87
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.13 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 87
tttttaagcc cacggccgnn cggccaccac agtgnggcag cgncgngcca tg                52

<210> SEQ ID NO 88
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.14 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 88
tttttaagcc cacaaaagnn cgggcagcac aggncgcnga ggncgngcca tg    52

<210> SEQ ID NO 89
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.15 sequence
<220> FEATURE:
<221> NAME/KEY: modified_base
<222> LOCATION: (15)..(15)
<223> OTHER INFORMATION: a, c, t, or g with a phenol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (35)..(35)
<223> OTHER INFORMATION: a, c, t, or g with a phenol functional group

<400> SEQUENCE: 89
tttttaacac gacgngacng tgagaggcac agtnnggggg cgtgggccca tg    52

<210> SEQ ID NO 90
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.16 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group
<220> FEATURE:
<221> NAME/KEY: modified_base
<222> LOCATION: (27)..(27)
<223> OTHER INFORMATION: a, c, t, or g with an amine functional group

<400> SEQUENCE: 90
tttttaacac gacagaccng tganggncga actccatgca tgtgggccca tg    52

<210> SEQ ID NO 91
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.17 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (24)..(24)
<223> OTHER INFORMATION: a, c, t, or g with an indol functional group

```
<220> FEATURE:
<221> NAME/KEY: modified_base
<222> LOCATION: (38)..(38)
<223> OTHER INFORMATION: a, c, t, or g with an indol functional group

<400> SEQUENCE: 91
tttttaagcc cacgccagnn cggncaacga actacggnga tgtgggccca tg              52

<210> SEQ ID NO 92
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.18 sequence
<220> FEATURE:
<221> NAME/KEY: modified_base
<222> LOCATION: (14)..(14)
<223> OTHER INFORMATION: a, c, t, or g with an amine functional group
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (27)..(27)
<223> OTHER INFORMATION: a, c, t, or g with an amine functional group

<400> SEQUENCE: 92
tttttaacac gacnanncng tgagncncga actgcgacaa cgtgggccca tg              52

<210> SEQ ID NO 93
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.19 sequence
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (27)..(27)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group
```

```
<400> SEQUENCE: 93
tttttaagcc cacaagcgnn cggcncncat agancgtnga cgtgggccca tg            52

<210> SEQ ID NO 94
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.20 sequence
<220> FEATURE:
<221> NAME/KEY: modified_base
<222> LOCATION: (17)..(17)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with an indol functional group
<220> FEATURE:
<221> NAME/KEY: modified_base
<222> LOCATION: (20)..(20)
<223> OTHER INFORMATION: a, c, t, or g with a phenol functional group
<220> FEATURE:
<221> NAME/KEY: modified_base
<222> LOCATION: (25)..(25)
<223> OTHER INFORMATION: a, c, t, or g with an amine functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (36)..(36)
<223> OTHER INFORMATION: a, c, t, or g with an indol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 94
tttttaagcc cacacgngnn cggancgcac agtnantggc agncgngcca tg            52

<210> SEQ ID NO 95
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.21 sequence
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (34)..(34)
<223> OTHER INFORMATION: a, c, t, or g with a phenol functional group
<220> FEATURE:
<221> NAME/KEY: modified_base
<222> LOCATION: (35)..(35)
<223> OTHER INFORMATION: a, c, t, or g with a phenol functional group
<220> FEATURE:
<221> NAME/KEY: modified_base
<222> LOCATION: (43)..(43)
<223> OTHER INFORMATION: a, c, t, or g with an amine functional group
<220> FEATURE:
<221> NAME/KEY: modified_base
<222> LOCATION: (46)..(46)
<223> OTHER INFORMATION: a, c, t, or g with a phenol functional group

<400> SEQUENCE: 95
```

```
tttttaagcc cacggggcng tgagcaacga acanngghcac agncgngcca tg          52
```

<210> SEQ ID NO 96
<211> LENGTH: 52
<212> TYPE: DNA
<213> ORGANISM: Artificial Sequence
<220> FEATURE:
<223> OTHER INFORMATION: Description of Artificial Sequence: Synthetic
      X-aptamer PEP 4.22 sequence
<220> FEATURE:
<221> NAME/KEY: modified_base
<222> LOCATION: (16)..(16)
<223> OTHER INFORMATION: a, c, t, or g with an indol functional group
<220> FEATURE:
<221> NAME/KEY: modified_base
<222> LOCATION: (19)..(19)
<223> OTHER INFORMATION: a, c, t, or g with a phenol functional group
<220> FEATURE:
<221> NAME/KEY: modified_base
<222> LOCATION: (38)..(38)
<223> OTHER INFORMATION: a, c, t, or g with an indol functional group

<400> SEQUENCE: 96

```
tttttaagcc cacggngcng tggaagccac agtacaangg agtgggccca tg          52
```

<210> SEQ ID NO 97
<211> LENGTH: 35
<212> TYPE: PRT
<213> ORGANISM: Homo sapiens

<400> SEQUENCE: 97

Trp Gly Asn Asn Gln Asp Gly Val Val Ala Ser Gln Pro Ala Arg Val
1               5                   10                  15

Val Asp Glu Arg Glu Gln Met Ala Ile Ser Gly Gly Phe Ile Arg Arg
            20                  25                  30

Val Thr Asn
        35

<210> SEQ ID NO 98
<211> LENGTH: 37
<212> TYPE: PRT
<213> ORGANISM: Homo sapiens

<400> SEQUENCE: 98

Leu Ala Asp Glu Ser Leu Glu Ser Thr Arg Arg Met Leu Gln Leu Val
1               5                   10                  15

Glu Glu Ser Lys Asp Ala Gly Ile Arg Thr Leu Val Met Leu Asp Glu
            20                  25                  30

Gln Gly Glu Gln Leu
        35

<210> SEQ ID NO 99
<211> LENGTH: 33
<212> TYPE: PRT
<213> ORGANISM: Homo sapiens

<400> SEQUENCE: 99

Gln Asn Arg Gln Ile Asp Arg Ile Met Glu Lys Ala Asp Ser Asn Lys
1               5                   10                  15

Thr Arg Ile Asp Glu Ala Asn Gln Arg Ala Thr Lys Met Leu Gly Ser
            20                  25                  30

Gly

<210> SEQ ID NO 100
<211> LENGTH: 24
<212> TYPE: PRT
<213> ORGANISM: Homo sapiens

<400> SEQUENCE: 100

Gln Asn Arg Gln Ile Asp Arg Ile Met Glu Lys Ala Asp Ser Asn Lys
1               5                   10                  15

Thr Arg Ile Asp Glu Ala Asn Gln
            20

<210> SEQ ID NO 101
<211> LENGTH: 225
<212> TYPE: PRT
<213> ORGANISM: Artificial Sequence
<220> FEATURE:
<223> OTHER INFORMATION: Description of Artificial Sequence: Synthetic
      modified human SNAP25 comprising a 5' myc tag and
      a 3' FLAG tag sequence

<400> SEQUENCE: 101

Met Glu Gln Lys Leu Ile Ser Glu Glu Asp Leu Met Ala Glu Asp Ala
1               5                   10                  15

Asp Met Arg Asn Glu Leu Glu Glu Met Gln Arg Arg Ala Asp Gln Leu
            20                  25                  30

Ala Asp Glu Ser Leu Glu Ser Thr Arg Arg Met Leu Gln Leu Val Glu
        35                  40                  45

Glu Ser Lys Asp Ala Gly Ile Arg Thr Leu Val Met Leu Asp Glu Gln
    50                  55                  60

Gly Glu Gln Leu Glu Arg Ile Glu Gly Met Asp Gln Ile Asn Lys
65                  70                  75                  80

Asp Met Lys Glu Ala Glu Lys Asn Leu Thr Asp Leu Gly Lys Phe Cys
                85                  90                  95

Gly Leu Cys Val Cys Pro Cys Asn Lys Leu Lys Ser Ser Asp Ala Tyr
            100                 105                 110

Lys Lys Ala Trp Gly Asn Asn Gln Asp Gly Val Val Ala Ser Gln Pro
        115                 120                 125

Ala Arg Val Val Asp Glu Arg Glu Gln Met Ala Ile Ser Gly Gly Phe
    130                 135                 140

Ile Arg Arg Val Thr Asn Asp Ala Arg Glu Asn Glu Met Asp Glu Asn
145                 150                 155                 160

Leu Glu Gln Val Ser Gly Ile Ile Gly Asn Leu Arg His Met Ala Leu
                165                 170                 175

Asp Met Gly Asn Glu Ile Asp Thr Gln Asn Arg Gln Ile Asp Arg Ile
            180                 185                 190

Met Glu Lys Ala Asp Ser Asn Lys Thr Arg Ile Asp Glu Ala Asn Gln
        195                 200                 205

Arg Ala Thr Lys Met Leu Gly Ser Gly Asp Tyr Lys Asp Asp Asp Asp
    210                 215                 220

Lys
225

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      Sequence N1, a FLAG tag

```
<400> SEQUENCE: 102

Asp Tyr Lys Asp Asp Asp Lys
1               5

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      Sequence N2, a myc tag

<400> SEQUENCE: 103

Glu Gln Lys Leu Ile Ser Glu Glu Asp Leu
1               5                   10
```